(12) United States Patent
Kim (10) Patent No.: US 11,224,350 B2
(45) Date of Patent: Jan. 18, 2022

(54) APPARATUS AND METHOD FOR DETECTING ARTIFACT OF BLOOD PRESSURE SIGNAL, AND COMPUTER READABLE RECORDING MEDIUM STORING THE METHOD

(71) Applicant: KOREA UNIVERSITY RESEARCH AND BUSINESS FOUNDATION, Seoul (KR)

(72) Inventor: Dong-Joo Kim, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 550 days.

(21) Appl. No.: 16/122,219

(22) Filed: Sep. 5, 2018

(65) Prior Publication Data

US 2019/0231196 A1  Aug. 1, 2019

(30) Foreign Application Priority Data

Jan. 26, 2018  (KR) .................. 10-2018-0010052

(51) Int. Cl.
*A61B 5/022* (2006.01)
*A61B 5/021* (2006.01)
(Continued)

(52) U.S. Cl.
CPC .............. *A61B 5/022* (2013.01); *A61B 5/021* (2013.01); *A61B 5/02108* (2013.01);
(Continued)

(58) Field of Classification Search
CPC ..... A61B 5/022; A61B 5/021; A61B 5/02108; A61B 5/7203; A61B 5/02028; A61B 5/0456; A61B 5/7267
(Continued)

(56) References Cited

U.S. PATENT DOCUMENTS 5,339,818 A * 8/1994 Baker ................ A61B 5/02156
600/490
5,533,511 A * 7/1996 Kaspari .............. A61B 5/02007
600/485
(Continued)

FOREIGN PATENT DOCUMENTS

JP          2008-541976 A    11/2008
KR   10-2009-0001146 A     1/2009
(Continued)

OTHER PUBLICATIONS

Lee, Soojeong, and Joon-Hyuk Chang. "Deep belief networks ensemble for blood pressure estimation." IEEE access 5 (2017): 9962-9972. (Year: 2017).*
(Continued)

*Primary Examiner* — David J. McCrosky
*Assistant Examiner* — Chanel J Jhin
(74) *Attorney, Agent, or Firm* — NSIP Law (57) ABSTRACT

A method for detecting an artifact of a blood pressure signal includes measuring consecutive signals of blood pressure in real time, dividing the consecutive signals into a plurality of unit waveforms by searching systolic starting points and peak points from the measured signals, determining two outputs by applying N consecutive unit waveforms among the plurality of unit waveforms as an input to a deep belief network (DBN), and determining whether the signal is an artifact or a normal signal by using the two determined outputs. According to the present disclosure, it is possible to minimize various false alarms of bio-signal streams which are measured in real time by automatically eliminating ABP artifacts using a deep belief network (DBN) which is one of deep neural network (DNN) models capable of learning causes and shapes of various types of artifacts together.

16 Claims, 8 Drawing Sheets

(51) Int. Cl.
    *A61B 5/00*     (2006.01)
    *A61B 5/02*     (2006.01)
    *A61B 5/352*     (2021.01)

(52) U.S. Cl.
    CPC ........ *A61B 5/7203* (2013.01); *A61B 5/02028* (2013.01); *A61B 5/352* (2021.01); *A61B 5/7267* (2013.01)

(58) Field of Classification Search
    USPC ........................................................ 600/485
    See application file for complete search history.

(56) References Cited

U.S. PATENT DOCUMENTS 9,560,977 B2     2/2017     Cohen et al.
2017/0332921 A1*   11/2017   Zirngibl ............. A61B 5/02125

FOREIGN PATENT DOCUMENTS

KR     10-2017-0048970 A     5/2017
KR     10-2017-0073051 A     6/2017

OTHER PUBLICATIONS

Shin, Hangsik, and Se Dong Min. "Feasibility study for the non-invasive blood pressure estimation based on ppg morphology: normotensive subject study." Biomedical engineering online 16.1 (2017): 10. (Year: 2017).*

Lee, Soojeong, et al., "Deep Belief Networks Ensemble for Blood Pressure Estimation." *IEEE access 5*, Jun. 28, 2017 (pp. 9962-9972).

Korean Office Action dated Jul. 16, 2019 in counterpart Korean Patent Application No. 10-2018-0010052 (6 pages in Korean).

Korean Notice of Allowance dated Jan. 29, 2020 in counterpart Korean Patent Application No. 10-2018-0010052 (2 pages in Korean).

* cited by examiner

APPARATUS AND METHOD FOR DETECTING ARTIFACT OF BLOOD PRESSURE SIGNAL, AND COMPUTER READABLE RECORDING MEDIUM STORING THE METHOD

CROSS-REFERENCE TO RELATED APPLICATIONS

This application claims the priority of Korean Patent Application No. 10-2018-0010052 filed on Jan. 26, 2018, in the Korean Intellectual Property Office, the disclosure of which is incorporated herein by reference.

BACKGROUND

Field

The present disclosure relates to a technology of automatically eliminating an artifact of an arterial pressure signal and diagnosing an abnormal prognosis.

Description of the Related Art

An arterial blood pressure (ABP) is one of the fundamental parameters used in clinical practice. It is a representative physiological-signal that is frequently collected and analyzed in clinical and research environments. The ABP signal not only provides cardiovascular information such as heart rate, rhythm, and arterial stiffness of the arterial blood vessels, but is also an important indicator of various pathological changes such as hypertension, hypotension, and arrhythmia.

The ABP signal may be contaminated by artifacts caused by various causes, such as patient motion, thrombus formation, cuff inflation and transducer flushing. The signal contaminated by artifacts can cause misdiagnosis of the patient's condition from the contaminated signal causes unnecessary aggressive or overactive treatment.

In a clinical environment, when an alarm in patient monitoring device is turned on, a medical manpower is needed to manually determine whether the alarm is due to the artifact or not. Then clinician diagnoses the physiological status of the patient and performs appropriate treatment. This procedure induces inefficiency of medical staff and observer variability in the environment where 50 to 80% of the ICU patient monitoring alarms is false alarms.

A conventional automatic artifact detection technology for solving this problem is a method of detecting signal abnormality by using a frequency band such as Wiener and Bayes filter to eliminate a signal in a frequency band different from a normal signal or detecting the signal abnormality by setting a threshold value for distinguishing the signal abnormality. The conventional automatic artifact detection technology is based on a specific model, so that it is difficult to eliminate various kinds of artifacts.

RELATED ART DOCUMENT

Patent Document (Patent Document 1) Korean Unexamined Patent Application Publication No. 10-2017-0073051 (Jun. 28, 2017) Title: Method and apparatus for measuring blood pressure (Patent Document 1) U.S. Pat. No. 9,560,977 (Dec. 4, 2014) Title of Invention: Method for estimating changes of cardiovascular indices using peripheral arterial blood pressure waveform

SUMMARY

An object to be achieved by the present disclosure is to provide an apparatus and a method for detecting artifacts of a blood pressure signal and a computer readable recording medium storing the same capable of controlling all types of artifacts by learning causes and shapes of various artifacts using a deep belief network.

According to an aspect of the present disclosure, there is provided a method for detecting artifacts of a blood pressure signal including: measuring consecutive signals of blood pressure in real time; dividing the consecutive signals into a plurality of unit waveforms by searching systolic starting points and peak points from the measured signals; determining two outputs by applying N consecutive unit waveforms among the plurality of unit waveforms as an input to a deep belief network (DBN); and determining whether the signal is an artifact or a normal signal by using the two determined outputs.

Here, the determination of the two outputs by the consecutive unit waveforms to the DBN may be performed by learning a morphological characteristic of the N unit waveforms.

Further, the determination of the two outputs by the consecutive unit waveforms to the DBN may be constituted by arranging the N unit waveforms as units of a visible layer, wherein the N unit waveforms are used as the input; and estimating units of each layer in a forward direction by adjusting weight values between adjacent layers from the visible layer to a final hidden layer.

Further, the method further includes estimating units of each layer in a backward direction by adjusting reverse weight values between the adjacent layers from the final hidden layer to the visible layer. The method further includes repeating the estimating of the units of each layer in the forward direction and the backward direction by adjusting the weight values and the reverse weight values. The weight values and the reverse weight values are determined that an error between the estimated unit and the inputted unit of the visible layer is minimal.

Further, the estimation of the units of each layer in the forward direction or the backward direction may be performed by estimating the unit using a probability calculated by the following Equation by adjusting the weight values or the reverse weight values.

$$P(v) = \frac{e^{-E(v,h)}}{\sum_h e^{-E(v,h)}}$$

(Here, v represents a visible layer, h represents a hidden layer, E represents an energy function of the joint configuration of (v, h), and P(h) can be calculated in the same manner)

The energy function E(v, h) may be determined by the following Equation.

$$E(v, h; \theta) = -\sum_{i=1}^{V}\sum_{j=1}^{H} w_{ij} v_i h_j - \sum_{i=1}^{V} b_i v_i - \sum_{j=1}^{H} a_j h_j$$

(Here, wij represents a weight value between an i-th layer and a j-th layer)

Further, the consecutive probability estimation between the respective layers may be calculated by the following Equation.

$$P(v) = \Sigma_h P(h|\theta) p(v|h,\theta)$$

Further, the weight value or the reverse weight value may be calculated by the following Equation.

$$\Delta w_{ij} = <v_i h_j>_{data} - <v_i h_j>_{model}$$

Further, the weight value or the reverse weight value may be modified by the following Equation.

$$\Delta w = \lambda \frac{\partial p(v)}{\partial w}$$

(Here, $\lambda$ as a learning rate has a value between 0 and 1.)

Further, the method may further include eliminating the signal to be determined as the artifact, after the determination of whether the signal is the artifact or the normal signal.

According to another exemplary embodiment of the present disclosure, there is provided a computer readable recording medium storing a program for executing a method for detecting an artifact of a blood pressure signal. The method includes fourth steps. A first step is to be receiving consecutive signals of blood pressure in real time. A second step is to be dividing the consecutive signals into a plurality of unit waveforms by searching systolic starting points and peak points from the inputted signals. A third step is to be determining two outputs by applying N consecutive unit waveforms among the plurality of unit waveforms as an input to a deep belief network (DBN). And, a fourth step is to be determining whether the signal is an artifact or a normal signal by using the two determined outputs.

According to yet another exemplary embodiment of the present disclosure, there is provided an apparatus for detecting an artifact of a blood pressure signal. The apparatus includes: a measurement unit for measuring consecutive signals of blood pressure in real time; and a control unit for dividing the consecutive signals into a plurality of unit waveforms by searching systolic starting points and peak points from the measured signals, determining two outputs by applying N consecutive unit waveforms among the plurality of unit waveforms as an input to a deep belief network (DBN), and determining whether the signal is an artifact or a normal signal by using the two determined outputs.

Further, the apparatus may further include a display for displaying the waveforms of the measure signal and whether the measured signal is an artifact or a normal signal.

Further, the control unit may eliminate the signal determined as the artifact from the measured signal and diagnose a prognosis using the signal in which the artifact is eliminated.

According to the present disclosure, it is possible to minimize various false alarms of bio-signal streams which are measured in real time by automatically eliminating ABP artifacts using a deep belief network (DBN) which is one of deep neural network (DNN) models capable of learning causes and shapes of various types of artifacts together.

BRIEF DESCRIPTION OF THE DRAWINGS

The above and other aspects, features and other advantages of the present disclosure will be more clearly understood from the following detailed description taken in conjunction with the accompanying drawings, in which.

DETAILED DESCRIPTION OF THE PREFERRED EMBODIMENT

The present disclosure may have various modifications and various exemplary embodiments, and specific exemplary embodiments will be illustrated in drawings and described in detail. However, the present disclosure is not limited to specific exemplary embodiments, and it should be understood that the present disclosure covers all the modifications, equivalents and replacements included within the idea and technical scope of the present disclosure.

Terms, such as first, second, A, and B may be used to describe various components and the components should not be limited by the terms. The terms are used only to discriminate one component from another component. For example, a first component may be referred to as a second component, and similarly, the second component may be referred to as the first component without departing from the scope of the present disclosure. A term 'and/or' includes a combination of a plurality of associated disclosed items or any item of the plurality of associated disclosed items.

It should be understood that, when it is described that a component is "connected to" or "accesses" the other component, the component may be directly connected to or access the other component or another component. In contrast, it should be understood that, when it is described that a component is "directly connected to" or "directly access" the other component, it is understood that no component is present between the component and the other component.

Terms used in the present application are used only to describe specific exemplary embodiments, and are not intended to limit the present disclosure. A singular form may include a plural form unless otherwise clearly meant in the context. In the present application, it should be understood that the term "include" or "have" indicates that a feature, a number, a step, an operation, a component, a part or a combination thereof described in the specification is present, but does not exclude a possibility of presence or addition of one or more other features, numbers, steps, operations, components, parts or combinations thereof, in advance.

Unless otherwise defined, all terms used herein including technological or scientific terms have the same meanings as those generally understood by a person with ordinary skill in the art. Terms defined in generally used dictionary should be construed to have meanings matching those in the context of a related art, and should not be construed in ideal or excessively formal meanings unless otherwise clearly defined in the present application.

Throughout the specification and all claims, when any part includes any component, unless specifically stated otherwise, it should be construed that other components are not excluded, but may be further included.

Hereinafter, preferred exemplary embodiments of the present disclosure will be described in detail with reference to the accompanying drawings.

Figure 1:
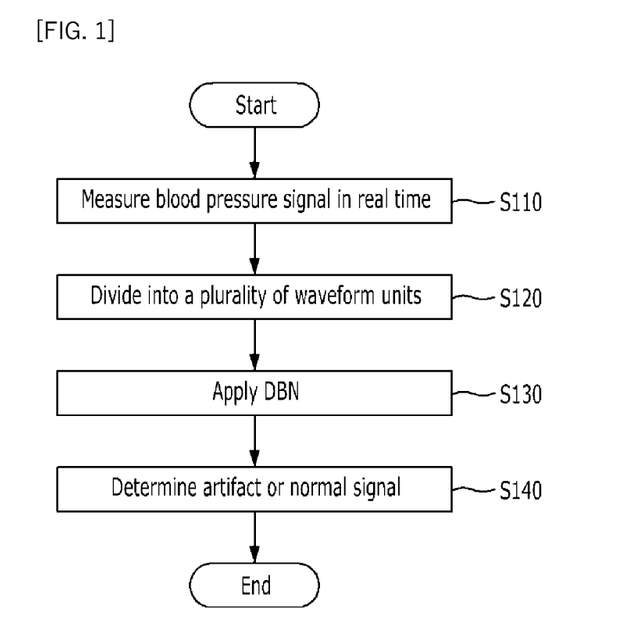
FIG. 1 is a flowchart of a method for detecting an artifact of a blood pressure signal according to an exemplary embodiment of the present disclosure.
Figure 2:
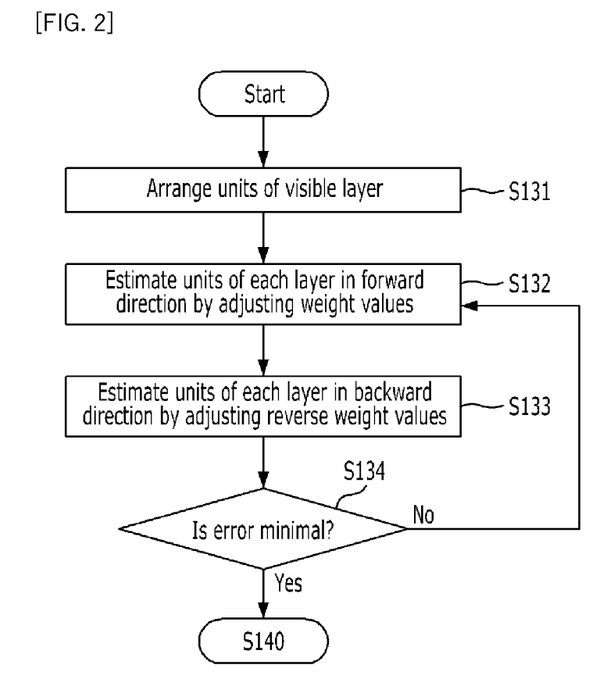
FIG. 2 is a flowchart of a DBN application method which is applied to the method for detecting an artifact of a blood pressure signal according to the exemplary embodiment of the present disclosure.

FIG. 1 is a flowchart of a method for detecting an artifact of a blood pressure signal according to an exemplary embodiment of the present disclosure and FIG. 2 is a flowchart of a DBN application method which is applied to the method for detecting an artifact of a blood pressure signal according to the exemplary embodiment of the present disclosure.

Referring to FIG. 1, a method of detecting an artifact of a blood pressure signal according to an exemplary embodiment of the present disclosure may be performed by steps of measuring a blood pressure signal in real time (S110), dividing the blood pressure signal into a plurality of unit waveforms (S120), determining two outputs by applying a DBN (S130), and determining whether the signal is an artifact or a normal signal (S140).

First, in the step of measuring a blood pressure signal in real time (S110), consecutive blood pressure signals may be measured in real time by a blood pressure measuring device worn on a patch attached to a body close to the heart of a subject or a forearm parallel the position of the heart. Generally, the blood pressure signal is represented in the form of repeated unit waveforms having a starting point and a peak point. In the case of a normal blood pressure signal, the same unit waveforms are repeatedly detected, but when artifacts are caused due to various causes such as a patient's motion or cuff inflation, a signal different from a normal unit waveform is detected. At this time, a technique is needed to distinguish the artifacts from the vascular diseases (for example, tachycardia, bradycardia, hypotension, and hypertension) that may occur in the patients.

In the step of dividing the measured signal into a plurality of unit waveforms (S120), the measured signal may be divided into unit waveforms by searching systolic starting points and peak points from the consecutively measured signal. Specifically, the systolic peak point is defined as a peak point having a maximum pressure value within a certain period of the peak points shown on the signal. The systolic peak point may be determined by a method of moving a time window of 1 second by 0.01 second, searching for the peak point having the maximum blood pressure value (a point whose absolute value of the slope is closest to '0') and then erasing the dicrotic points. Next, the systolic starting point may be selected as a point at which a pressure value is lowest between two consecutive systolic peak points and before the slope increases rapidly. Two adjacent systolic starting points may be divided into one unit waveform.

In the step of applying the DBN (S130), N consecutive unit waveforms of the plurality of unit waveforms may be input and applied to a deep belief network (DBN) to determine two outputs. A detailed procedure of applying the DBN will be described below with reference to FIG. 2.

In the step of determining whether the signal is the artifact or the normal signal (S140), when a first signal value is large, the first signal value is determined as the artifact by using the two outputs determined. If a second signal value is large, the second signal value may be determined as a normal signal. At this time, the two outputs are obtained by learning morphological characteristics of the unit pulses.

Referring to FIG. 2, the DBN application method which is applied to the method for detecting an artifact of a blood pressure signal according to the exemplary embodiment of the present disclosure includes arranging units in a visible layer (S131), and estimating units of each layer in a forward direction by adjusting a weight value (S132).

Further, the DBN application method may be used for estimating units of each layer in a backward direction by adjusting a reverse weight value after measuring the units of each layer in the forward direction (S133). The method comprises determining whether an error of the units of the estimated visible layer becomes minimum by applying the units inputted to the visible layer and the reverse weight value. And the method further comprises detecting an output of a final hidden layer as an artifact by stopping the DBN application if the error is the minimum (Yes) (S140). If the error is not the minimum (No), the weight value adjustment in the forward direction and the reverse weight value adjustment in the backward direction may be sequentially repeated (S132 to S133). At this time, the criterion that the error is minimum can be set in advance.

Specifically, the N unit waveforms are input to be disposed as the units of the visible layer and weight values between adjacent layers from the visible layer to the final hidden layer are adjusted to sequentially estimate units of each layer in a forward direction. At this time, respective units of the same layer are not connected to each other, but may be connected to units of the adjacent layers. After estimating the units of each layer in the forward direction, reverse weight values between adjacent layers from the final hidden layer to the visible layer are adjusted to estimate units of each layer in the backward direction. It is possible to repeat the process of estimating the units of each layer in the forward direction and the backward direction by adjusting the weight value and the reverse weight value so that the error between the input unit and the estimated unit is minimized.

The units of each layer may be estimated in the forward direction or the backward direction by using a probability calculated by Equation (1) by adjusting the weight value or the reverse weight value. Here, v represents a visible layer, h represents a hidden layer, E represents an energy function of the joint configuration of (v, h), and P(h) can be calculated in the same manner.

$$P(v) = \frac{e^{-E(v,h)}}{\sum_{h} e^{-E(v,h)}} \quad \text{[Equation 1]}$$

The energy function E(v, h) may be determined by Equation 2. Here, wij represents a weight value between an i-th layer and a j-th layer.

$$E(v, h; \theta) = -\sum_{i=1}^{V}\sum_{j=1}^{H} w_{ij} v_i h_j - \sum_{i=1}^{V} b_i v_i - \sum_{j=1}^{H} a_j h_j \quad \text{[Equation 2]}$$

In addition, the consecutive probability estimation between the respective layers may be calculated by Equation 3, and a unit value of each layer may be calculated according to Equation 3 based on the unit value of the visible layer.

$$P(v) = \Sigma_h P(h|\theta) p(v|\theta) \quad \text{[Equation 2]}$$

In addition, the weight value or the reverse weight value connecting each layer may be calculated by Equation 4, and the weight value or the reverse weight value may be modified by Equation 5.

$$\Delta w_{ij} = \langle v_i h_j \rangle_{data} - \langle v_i h_j \rangle_{model} \quad \text{[Equation 4]}$$

$$\Delta w = \lambda \frac{\partial p(v)}{\partial w} \quad \text{[Equation 5]}$$

Here, λ as a learning rate has a value between 0 and 1.

After determining whether the signal is the artifact or the normal signal using the two outputs determined as described above, it is possible to eliminate a signal determined as the artifact and determine whether a vascular disease has occurred.

Figure 3:
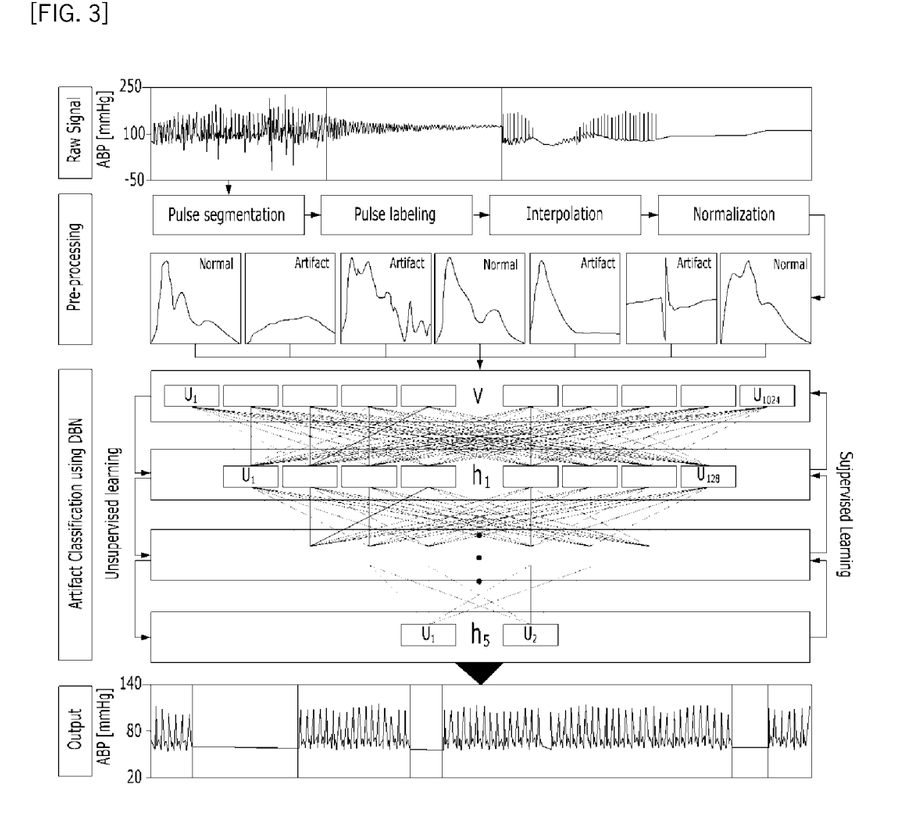
FIG. 3 is a diagram of a blood pressure signal to which the method for detecting an artifact of a blood pressure signal according to the exemplary embodiment of the present disclosure.

FIG. 3 is a diagram of a blood pressure signal to which the method for detecting an artifact of a blood pressure signal according to the exemplary embodiment of the present disclosure is applied.

Referring to FIG. 3, the method of detecting an artifact of a blood pressure signal according to the exemplary embodiment of the present disclosure may perform a pre-processing process of detecting a raw signal of an arterial blood pressure. The method further comprises dividing the raw signal into unit pulses, and attaching a label of a normal signal or an artifact depending on a morphological characteristic of each unit pulse. At this time, the unit pulse may be normalized and represented.

Next, the artifacts may be classified by applying DBN. It is possible to determine the output values by arranging N units on the visible layer and sequentially estimating units of adjacent hidden layers. As described above, the final output value may be determined by repeating the forward and backward estimation. The final output value may be used to eliminate artifact sections from the measured signal.

Hereinafter, a process of dividing unit pulses from an arterial blood pressure signal and detecting artifacts by applying the DBN will be described in detail.

Figure 4:
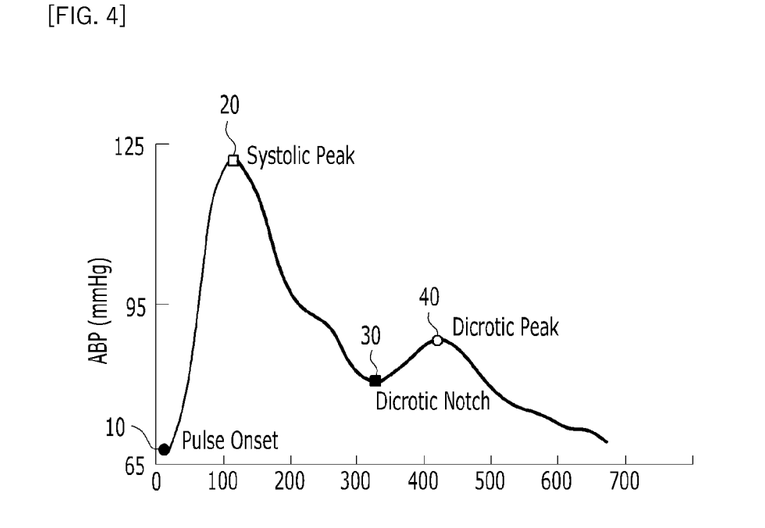
FIG. 4 is a diagram for describing a method of dividing unit waveforms which is applied to the method for detecting an artifact of a blood pressure signal according to the exemplary embodiment of the present disclosure.
Figure 5:
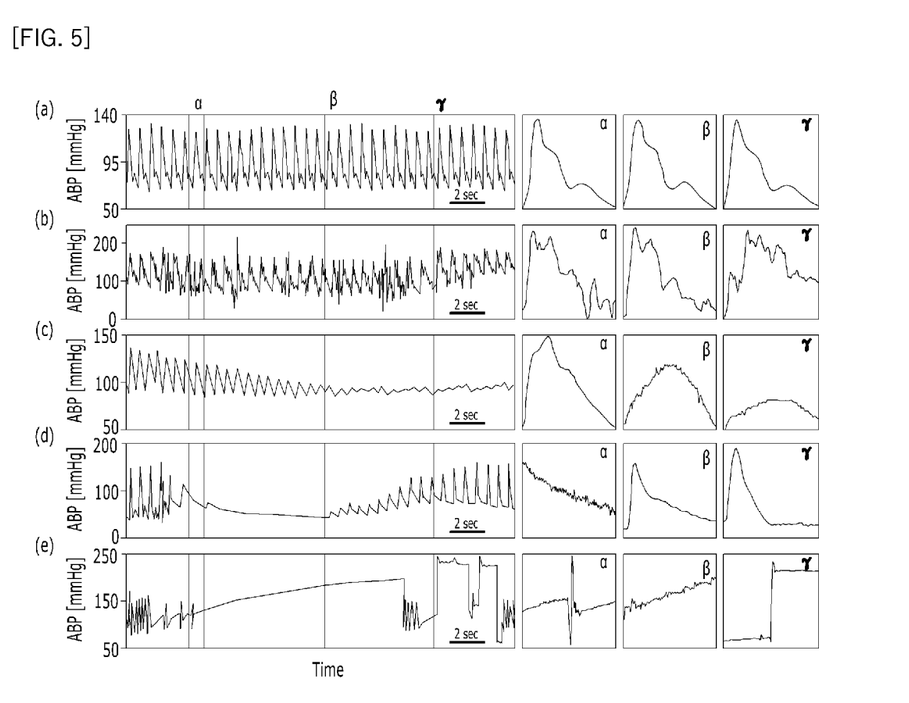
FIG. 5 is a diagram for describing a method of dividing unit waveforms between a normal arterial blood pressure signal and an arterial blood pressure signal including various artifacts, which is applied to the method for detecting an artifact of a blood pressure signal according to the exemplary embodiment of the present disclosure.

FIG. 4 is a diagram for describing a method of dividing unit waveforms which is applied to the method for detecting an artifact of a blood pressure signal according to the exemplary embodiment of the present disclosure. FIG. 5 is a diagram for describing a method of dividing unit waveforms between a normal arterial blood pressure signal and an arterial blood pressure signal including various artifacts, which is applied to the method for detecting an artifact of a blood pressure signal according to the exemplary embodiment of the present disclosure.

Referring to FIG. 4, a feature point of the arterial blood pressure waveform includes a pulse onset 10 of the waveform, a systolic peak point 20, a dicrotic notch 30, and a dicrotic peak 40. Such a feature point of the arterial blood pressure waveform is closely associated with the blood circulation.

Specifically, the pulse onset 10 of the waveform is associated with a point where the aortic valve is opened, the systolic peak point 20 reflects emission of the blood when the ventricular pressure exceeds the arterial pressure to open the meniscus and the arterial wave reflection, and the dicrotc notch 30 is associated with the aortic valve closure.

The unit waveforms may be divided based on the pulse onsets 10 between the systolic peak points 20 of the waveform among the above feature points.

Referring to FIG. 5, a process of extracting unit pulses in a specific section of an arterial blood pressure signal a having no artifact is as described above. However, since the starting points and the peak points of arterial blood pressure signals b to e including the artifacts are unclear, the unit pulse may be divided into the same time period as the unit pulse of the normal signal.

Figure 6:
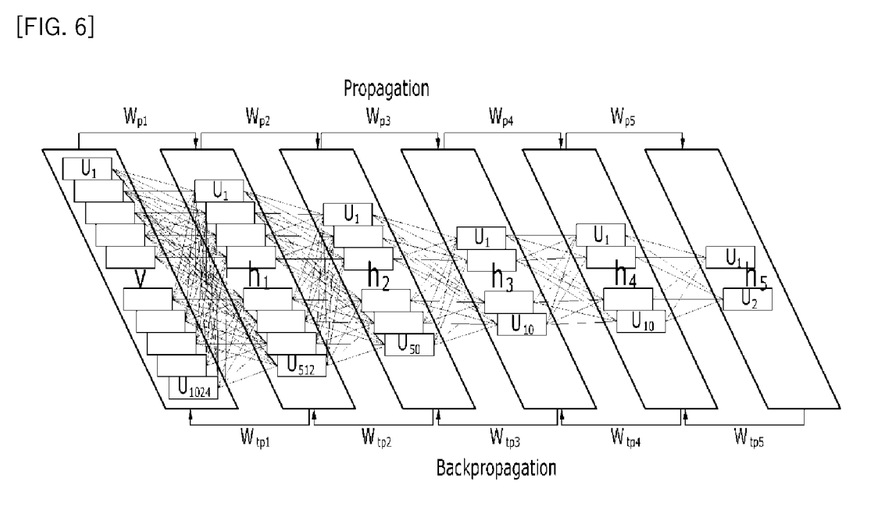
FIG. 6 is a diagram for describing a DBN application method which is applied to the method for detecting an artifact of a blood pressure signal according to the exemplary embodiment of the present disclosure.

FIG. 6 is a diagram for describing a DBN application method which is applied to the method for detecting an artifact of a blood pressure signal according to the exemplary embodiment of the present disclosure.

Referring to FIG. 6, 1024 unit waveforms are arranged in a visible layer v as units $u_1$ to $u_{1024}$, and weight values $W_{p1}$, $W_{p2}$, $W_{p3}$, $W_{p4}$, $W_{p5}$ are adjusted to estimate units of respective layers $h_1$, $h_2$, $h_3$, $h_4$, and $h_5$. After propagation, a process of performing backpropagation is repeated by adjusting reverse weight values $W_{bp1}$, $W_{bp2}$, $W_{bp3}$, $W_{bp4}$, and $W_{bp5}$ to learn output values $u_1$ and $u_2$ of the final hidden layer $h_5$.

When the output value $u_1$ is larger than the output value $u_2$ by using the output values $u_1$ and $u_2$ of the final hidden layer $h_5$, it is determined as an artifact, and when the output value $u_1$ is smaller than the output value $u_2$, it is determined as a normal signal.

Figure 7:
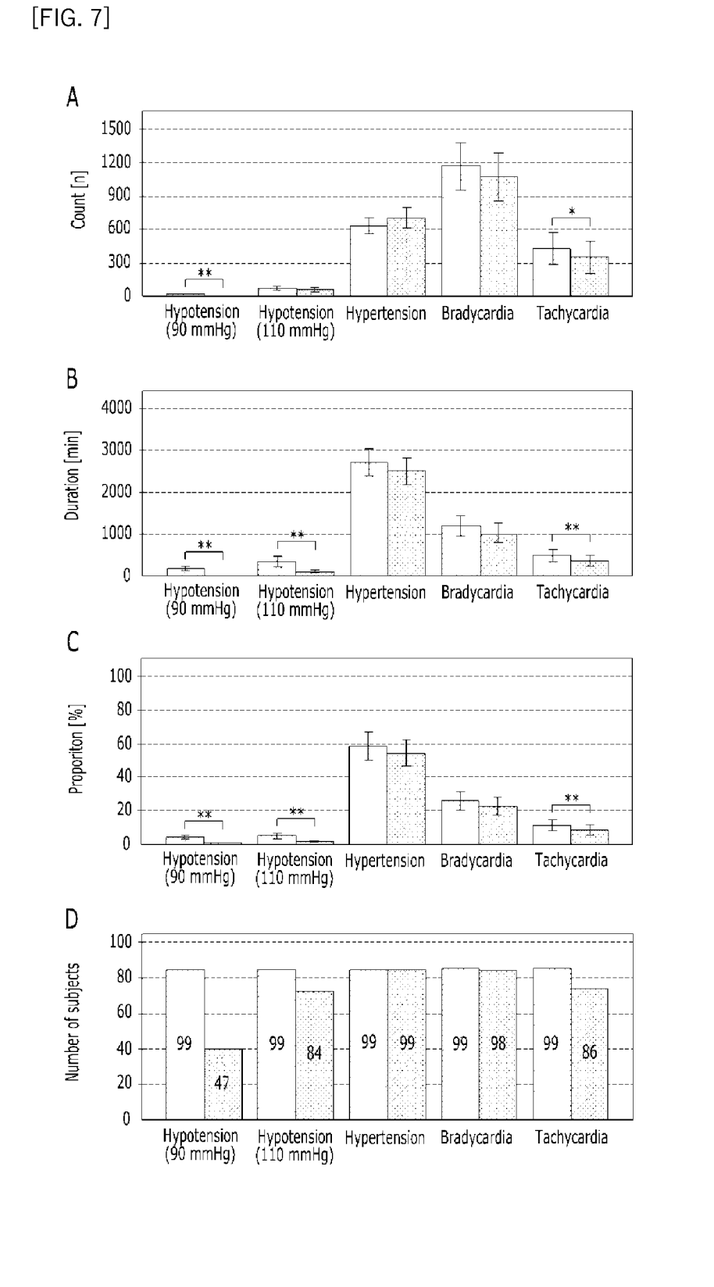
FIGS. 7 and 8 are diagrams illustrating comparing occurrence rates of alarms before and after eliminating artifacts using the method for detecting an artifact of a blood pressure signal according to the exemplary embodiment of the present disclosure.
Figure 8:
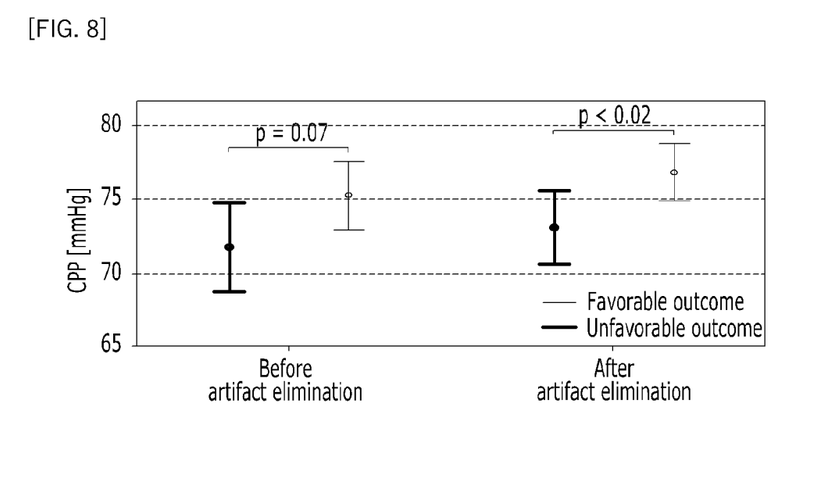

FIGS. 7 and 8 are diagrams illustrating comparing occurrence rates of alarms before and after eliminating artifacts using the method for detecting an artifact of a blood pressure signal according to the exemplary embodiment of the present disclosure.

FIG. 7 illustrates the number of times, the duration, the total ratio, and the number of times of hypotension, hypertension, tachycardia, and bradycardia which are measured in the case where the artifacts are not eliminated (in a black bar graph) and in the case where the artifact are eliminated (in a gray bar graph).

When artifacts are eliminated, it can be seen that the number of false alarms of the hypotension, the hypertension, the tachycardia, and the bradycardia is reduced.

FIG. 8 illustrates average CPP differences measured in the case where the artifacts are not eliminated and in the case where the artifacts are eliminated. It can be seen that when the artifacts are not eliminated, the prognostic capacity of CPP for patients with traumatic brain injury is improved from p=0.07 to p=0.02.

Figure 9:
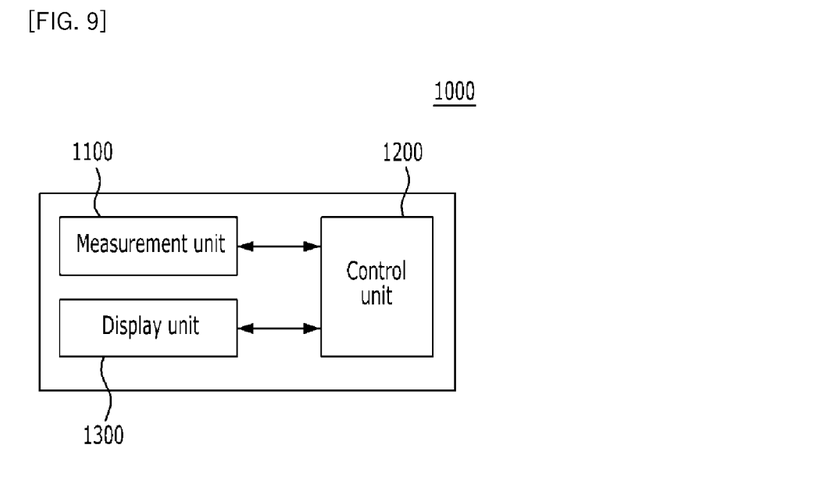
FIG. 9 is a schematic block diagram of an apparatus for detecting an artifact of a blood pressure signal according to another exemplary embodiment of the present disclosure.

FIG. 9 is a schematic block diagram of an apparatus for detecting an artifact of a blood pressure signal according to another exemplary embodiment of the present disclosure.

Referring to FIG. 9, an apparatus 1000 for detecting an artifact of a blood pressure signal according to another exemplary embodiment of the present disclosure includes a measurement unit 1100 and a control unit 1200. In addition, the apparatus 1000 for detecting an artifact of a blood pressure signal may further include a display unit 1300.

The measurement unit 1100 can measure consecutive signals of blood pressure in real time. For example, the measurement unit 1100 may be a patch attached to the vicinity of the heart.

The control unit 1200 may searches for a systolic start point and a systolic peak point from the measured signal to divide consecutive signals into a plurality of unit waveforms. The control unit 1200 may apply N consecutive unit waveforms among the plurality of unit waveforms as an input to a deep belief network (DBN) to determine two outputs. The control unit 1200 may determine whether the signal is an artifact or a normal signal by using the two determined outputs. The control unit 1200 represents an access processor (AP), a CPU, or other processors, and may be implemented as a hardware module or software. The control unit 1200 may eliminate the signal determined as the artifact from the measured signal and diagnose the prognosis using the signal in which the artifact is eliminated.

The display unit 1300 may display whether the waveform of the measured signal and the measured signal are artifacts or normal signals, and display the diagnosis results together.

According to yet another exemplary embodiment of the present disclosure, there is provided a computer readable recoding medium storing the method for detecting an artifact of a blood pressure signal, including steps of receiving consecutive signals of the blood pressure in real time, searching systolic starting points and peak points from the input signal to divide the consecutive signals into a plurality of unit waveforms, determining two outputs by applying N consecutive unit waveforms among the plurality of unit waveforms as an input to a deep belief network (DBN), and determining whether the signal is an artifact or a normal signal by using the determined two outputs.

As described above, a program for executing the method for detecting the artifact of the blood pressure signal according to yet another exemplary embodiment of the present disclosure may include codes coded by a computer language such as C, C++, JAVA, or a machine language which can be read by a processor (CPU) of the computer. These codes may further include memory reference related codes for whether additional information or media required for executing the functions by the processor of the computer should be referred to at any location (address, house number) of the internal or external memory of the computer.

A functional program for implementing the present disclosure and codes and code segments related thereto may be easily inferred or changed by programmers in the technical field of the present disclosure in consideration of a system environment of the computer that reads the recording medium and executes the program. The computer readable recording medium storing the program includes a ROM, a RAM, a CD-ROM, a magnetic tape, a floppy disk, an optical media storage device, and the like.

Hereinabove, even if it is described that all of components constituting the exemplary embodiment of the present disclosure are coupled as a single unit or coupled to be operated as a single unit, the present disclosure is not necessarily limited to the exemplary embodiment. That is, among the components, all the components may be selectively coupled to at least one to be operated within the scope of the object of the present disclosure. In addition, although each of the constituent elements may be implemented as an independent hardware, some or all of the constituent elements may be selectively combined with each other, so that they can be implemented as a computer program having one or more program modules for executing some or all of the functions combined in one or multiple hardware. Codes and code segments constituting the computer program can be easily inferred by those skilled in the art. The computer program is stored in computer readable media to be read and executed by the computer and thus the exemplary embodiment of the present disclosure can be implemented. The storage media of the computer program may include a magnetic recording medium, an optical recording medium, or the like.

Although the exemplary embodiments of the present disclosure have been described in detail with reference to the accompanying drawings, the present disclosure is not limited thereto and may be embodied in many different forms without departing from the technical concept of the present disclosure. Therefore, the exemplary embodiments of the present disclosure are provided for illustrative purposes only but not intended to limit the technical concept of the present disclosure. The scope of the technical concept of the present disclosure is not limited thereto. The protective scope of the present disclosure should be construed based on the following claims, and all the technical concepts in the equivalent scope thereof should be construed as falling within the scope of the present disclosure.

What is claimed is:

1. A method for detecting an artifact of a blood pressure signal, the method comprises:
    measuring consecutive signals of blood pressure in real time by a patch;
    dividing, by a processor, the consecutive signals into a plurality of unit waveforms by searching systolic starting points and peak points from the measured consecutive signals;
    determining, by the processor, two outputs by applying N consecutive unit waveforms among the plurality of unit waveforms as an input to a deep belief network (DBN); and
    determining, by the processor, whether the consecutive signals are artifacts or normal signals by using the two determined outputs,
    wherein the processor divides two adjacent systolic starting points into one unit waveform,
    wherein the processor arranges the N consecutive unit waveforms on a visible layer and sequentially estimates units of adjacent hidden layers,
    wherein the processor estimates units of each layer in a forward direction by adjusting weight values from the visible layer to a final hidden layer, and the processor estimates the units of each layer in a backward direction by adjusting reverse weight values from the final hidden layer to the visible layer,
    wherein the processor determines two unit values of the final hidden layer as the two determined outputs, and
    wherein the processor determines that: the consecutive signals are artifacts when a first output value of the final hidden layer is greater than a last output value of the final hidden layer; or the consecutive signals are normal signals when the first output value of the final hidden layer is smaller than the last output value of the final hidden layer.

2. The method of claim 1, wherein the determining the two outputs is performed by determining the two outputs by learning a morphological characteristic of the N consecutive unit waveforms.

3. The method of claim 1, wherein the determining the two outputs is constituted by
    arranging the N consecutive unit waveforms as units of the visible layer, wherein the N consecutive unit waveforms are used as the input; and estimating the units of each layer in the forward direction by adjusting weight values between adjacent layers from the visible layer to the final hidden layer.

4. The method of claim 3, further comprising:
after the estimating the units of each layer in the forward direction by adjusting the weight values between the adjacent layers from the visible layer to the final hidden layer,
estimating the units of each layer in a backward direction by adjusting reverse weight values between the adjacent layers from the final hidden layer to the visible layer; and
repeating the estimating the units of each layer in the forward direction and the backward direction by adjusting the weight values and the reverse weight values such that an error between the estimated units of the visible layer and the inputted units of the visible layer is minimal.

5. The method of claim 4, wherein the estimating the units of each layer in the forward direction or the backward direction is performed by estimating the units of each layer using a probability calculated by the following Equation by adjusting the weight values or the reverse weight values:

$$P(v) = \frac{e^{-E(v,h)}}{\sum_h e^{-E(v,h)}}$$

wherein v represents a visible layer, h represents a hidden layer, E represents an energy function of a joint configuration of (v, h), and P(h) can be calculated in the same manner.

6. The method of claim 4, wherein the weight values or the reverse weight values are calculated by the following Equation:

$$\Delta w_{ij} = <v_i h_j>_{data} - <v_i h_j>_{model}.$$

7. The method of claim 3, wherein the estimating the units of each layer in the forward direction or the backward direction is performed by estimating the units of each layer using a probability calculated by the following Equation by adjusting the weight values or the reverse weight values:

$$P(v) = \frac{e^{-E(v,h)}}{\sum_h e^{-E(v,h)}}$$

wherein v represents the visible layer, h represents the hidden layer, E represents an energy function of a joint configuration of (v, h), and P(h) can be calculated in the same manner.

8. The method of claim 7, wherein the energy function E(v, h) is determined by the following Equation:

$$E(v, h; \theta) = -\sum_{i=1}^{V}\sum_{j=1}^{H} w_{ij} v_i h_j - \sum_{i=1}^{V} b_i v_i - \sum_{j=1}^{H} a_j h_j$$

wherein wij represents a weight value between an i-th layer and a j-th layer.

9. The method of claim 8, wherein a consecutive probability estimation between respective layers is calculated by the following Equation:

$$P(v) = \Sigma_h P(h|\theta) p(v|h,\theta).$$

10. The method of claim 7, wherein the weight values or the reverse weight values are calculated by the following Equation:

$$\Delta w_{ij} = <v_i h_j>_{data} - <v_i h_j>_{model}.$$

11. The method of claim 10, wherein the weight values or the reverse weight values are modified by the following Equation:

$$\Delta w = \lambda \frac{\partial p(v)}{\partial w}$$

wherein λ as a learning rate has a value between 0 and 1.

12. The method of claim 1, further comprising:
after the determining whether the consecutive signals are the artifacts or the normal signals by using the two determined outputs,
eliminating signals determined as the artifacts.

13. A non-transitory computer readable recording medium storing a program for executing a method for detecting an artifact of a blood pressure signal comprising,
receiving consecutive signals of blood pressure in real time by a patch, dividing the consecutive signals into a plurality of unit waveforms by searching systolic starting points and peak points from the received consecutive signals by a processor, determining two outputs by applying N consecutive unit waveforms among the plurality of unit waveforms as an input to a deep belief network (DBN) by the processor, and determining whether the consecutive signal are artifacts or normal signals by comparing the two determined outputs by the processor,
wherein the two Outputs are determined as two unit values of a hidden layer by repeating propagation and backpropagation in the DBN,
wherein the processor divides two adjacent systolic starting points into one unit waveform, and
wherein the processor determines that: the consecutive signals are artifacts when a first output value of the two determined outputs is greater than a last output value of the two determined outputs; or the consecutive signals are normal signals when the first output value of the two determined outputs is smaller than the last output value of the two determined outputs.

14. An apparatus for detecting an artifact of a blood pressure signal, the apparatus comprising:
a patch for measuring consecutive signals of blood pressure in real time; and
a processor for dividing the consecutive signals into a plurality of unit waveforms by searching systolic starting points and peak points from the measured consecutive signals, determining two outputs by applying N consecutive unit waveforms among the plurality of unit waveforms as an input to a deep belief network (DBN), and determining whether the consecutive signals are artifacts or normal signals by comparing the two determined outputs,
wherein the processor divides two adjacent systolic starting points into one unit waveform, wherein, the processor arranges the N consecutive unit waveforms on a visible layer and sequentially estimates units of adjacent hidden layers, wherein, the processor estimates units of each layer in a forward direction by adjusting weight values from the visible layer to a final hidden layer, and the processor estimates the units of each layer in a backward direction by adjusting reverse weight values from the final hidden layer to the visible layer, wherein, the processor determines two unit values of the final hidden layer as the two determined outputs, and wherein the processor determines that: the consecutive signals are artifacts when a first output value of the two determined outputs is greater than a last output value of the two determined outputs; or the consecutive signals are normal signals when the first output value of the two determined outputs is smaller than the last output value of the two determined outputs.

15. The apparatus of claim 14, further comprising:

a display for displaying the plurality of unit waveforms of the consecutive signals and whether the consecutive signals are artifacts or normal signals.

16. The apparatus of claim 14, wherein the processor eliminates signals determined as the artifacts from the consecutive signals and diagnoses a prognosis using signals in which the artifacts are eliminated.

* * * * *